United States Patent [19]

Angel

[11] Patent Number: 4,473,078
[45] Date of Patent: Sep. 25, 1984

[54] CARDIAC ARRHYTHMIA ANALYSIS SYSTEM

[75] Inventor: James H. Angel, Aurora, Oreg.

[73] Assignee: Cardiac Resuscitator Corporation, Wilsonville, Oreg.

[21] Appl. No.: 381,644

[22] Filed: May 24, 1982

[51] Int. Cl.$^3$ .......................... A61N 1/36; A61B 5/04
[52] U.S. Cl. ........................ 128/419 D; 128/419 PG; 128/705
[58] Field of Search ............ 128/419 D, 419 PG, 702, 128/704, 705, 706, 703

[56] References Cited

U.S. PATENT DOCUMENTS

| | | | |
|---|---|---|---|
| Re. 30,750 | 9/1981 | Black | 128/419 D |
| 3,707,959 | 1/1973 | Wilton-Daves | 128/2.06 A |
| 3,841,315 | 10/1974 | Kopp | 128/2.06 A |
| 3,878,833 | 9/1975 | Arneson | 128/2.06 A |
| 3,927,663 | 12/1975 | Russell | 128/2.06 A |
| 3,998,214 | 12/1976 | Garrison | 128/2.06 A |
| 4,184,493 | 1/1980 | Langer | 128/419 D |
| 4,192,318 | 3/1980 | Dam | 128/708 |
| 4,237,903 | 12/1980 | Hoffman | 128/708 |
| 4,291,699 | 9/1981 | Geddes | 128/419 D |
| 4,393,877 | 7/1983 | Imran | 128/705 |

OTHER PUBLICATIONS

National Semiconductor Linear Applications Handbook (1980) pp. AN208 and AN20-9.

Primary Examiner—Kyle L. Howell
Assistant Examiner—Deidre A. Foley
Attorney, Agent, or Firm—Chernoff, Vilhauer, McClung, Birdwell & Stenzel

[57] ABSTRACT

A method and apparatus for analyzing cardiac electrical activity and other life signs, and triggering a therapeutic current. A signal representative of cardiac electrical activity is analyzed by two distinct analog circuits and a logic protocol is provided to identify cardiac arrhythmia based on the outputs of the circuits and the presence or absence of respiration. One circuit employs comparison of the electrical signal with a previous peak value thereof, and is characterized by its tendency to double-count some QRS complexes. The other circuit compares the sum of the rectified and low-pass filtered signal plus the derivative of the signal to a reference level, and compares the rectified and filtered signal to a threshold level, to identify QRS complexes while largely ignoring ventricular fibrillation. Defibrillation is triggered if either the second circuit produces output pulses greater than or equal to 200 pulses per minute, or the first circuit produces output pulses greater than 200 pulses per minute and the second circuit produces pulses at a rate less than half the pulse rate of the first circuit. Pacing is triggered if both circuits produce pulses at a rate less than 25 pulses per minute. Tachycardia and/or ventricular fibrillation must be apparently identified several times, and lack of respiration must be established, within a predetermined time period in order for defibrillation to be triggered. Defibrillation is inhibited as a result of interference which could produce unreliable measurements.

3 Claims, 15 Drawing Figures

CARDIAC ARRHYTHMIA ANALYSIS SYSTEM

This invention relates to methods and apparatus for monitoring cardiac electrical activity and other life signs and triggering the application of appropriate therapeutic electrical current.

In order to save heart attack victims suffering from cardiac arrest and arrhythmias such as bradycardia (slowness of the heart beat), tachycardia (excessively rapid heart beat), and ventricular fibrillation (rapid uncoordinated fibrillary contraction of the ventricular muscle), systems have been developed for monitoring cardiac electrical activity and other life signs such as respiration, and automatically administering appropriate therapeutic electrical currents to a patient to stimulate normal cardiac activity. One such system is described in Diack et al. U.S. Pat. No. Re. 30,750 for "Cardiac Resuscitator and Monitoring Apparatus", reissued Sept. 29, 1981, and hereby incorporated by reference in its entirety.

In such systems means must be provided for accurately identifying from an electrical signal produced by the patient representative of cardiac electrical activity (hereinafter referred to for convenience as an electro-cardiac signal), in conjunction with other life signs such as the presence or absence of respiration, the existence and type of cardiac arrhythmia. Because of the complexity of the electro-cardiac signal and the variations that can occur therein depending upon the nature of the arrhythmia, accurate identification depends upon the analysis techniques utilized and the circuitry employing those techniques.

It has been found by the applicant that one previously utilized system for analyzing an electro-cardiac signal to identify the nature of an arrhythmia has not been as satisfactory as desired. That system basically employs signal conditioning by bandpass filtering, identification of waveform peaks, and comparison of the waveform amplitude to the waveform peaks to produce output pulses generally corresponding to ventricular contractions in the case of a coordinated muscular contraction or to the extremes of the oscillatory electrical activity associated with ventricular fibrillation. However, it has been found that this technique cannot discriminate between some types of cardiac arrhythmias and true ventricular fibrillation with the result that, in the presence of some unusual QRS complexes (waveforms associated with coordinated muscular contraction), the system "double counts", that is, indicates a heart beat rate twice as high as the actual ventricular contraction rate.

Other systems for identifying characteristics of an electro-cardiac signal are also known. For example, Arneson et al. U.S. Pat. No. 3,878,833 discloses a system utilizing peak detection and comparison with respect to the derivative of the electro-cardiac signal and a timing circuit for measuring the duration of an R wave candidate pulse. Another approach is illustrated by Russell et al. U.S. Pat. No. 3,927,663, where the amplitude of the rectified electro-cardiac signal is compared to a percentage thereof. A further approach is illustrated by Langer et al. U.S. Pat. No. 4,184,493 which utilizes differentiation of the electro-cardiac signal followed by threshold detection. However, it is believed that none of these provides a satisfactory indication of the existence and nature of various cardiac arrhythmias.

In systems such as these it is also important to reject interfering signals resulting, for example, from touching or moving the patient while sensing electrodes are attached, in order to obtain a reliable analysis. Many electro-cardiac signal analysis circuits utilize conventional filtering techniques to reject or reduce noise and other interfering signals, but there has been a need to accomplish this more effectively. Similarly, reliance on a single indication of cardiac arrhythmia is less accurate than desired due to the possibility of an erroneous indication from a momentary deviation in cardiac behavior which does not warrant the application of therapeutic current; yet, it is important that the identification of life-threatening arrhythmia be accomplished as quickly as possible to avoid damage to unoxygenated tissue and even death.

The application of a defibrillation current to a patient requires the release of a large amount of electrical energy to the patient in a short period of time. As a practical matter this is typically accomplished by the discharge of a relatively large capacitor which, for purposes of safety, is charged just prior to administration of the defibrillation current. Again, however, it is important that a system of this type minimize the time between arrhythmia identification and defibrillation, so it is desirable to reduce or eliminate the effective time for charging the capacitor.

Accordingly, it can be seen that there is a need for improvement in cardiac monitoring and resuscitation systems, particularly in the techniques for analysis of the electro-cardiac signal for triggering of a therapeutic current.

Some other technical references which may be of general interest are: Garrison U.S. Pat. No. 3,998,214; Wilton-Davies U.S. Pat. No. 3,707,959; Dam et al. U.S. Pat. No. 4,192,318; Hofmann U.S. Pat. No. 4,237,903 and Kopp U.S. Pat. No. 3,841,315.

SUMMARY OF THE INVENTION

The afore-described drawbacks and limitations of prior art cardiac arrhythmia analysis systems are overcome, and additional advantages are achieved, in the present invention by the provision of a novel arrhythmia analysis method and apparatus for implementing the same, including a novel logic protocol for rapidly selecting and triggering therapeutic current while reducing the likelihood of error in identification of arrhythmia.

A principal, and the first developed, part of the system is a new circuit for detection of a QRS complex in an electro-cardiac signal. In the circuit the electro-cardiac signal is first filtered to remove dc, and very low and high frequency elements. Thereafter, the filtered electro-cardiac signal is differentiated and the derivative is summed with a scaled signal derived from the lowpass filtered absolute value of the same electro-cardiac signal. This sum is then compared to a reference level and if the sum is less that that reference level a resultant signal is produced indicating that the portion of the electro-cardiac signal being examined qualifies as a possible QRS event. Simultaneously, the filtered absolute value signal is compared to a threshold level and if the filtered absolute value signal exceeds the threshold coincident with the occurrence of the aforementioned resultant signal a pulse if produced indicative of the occurrence of a QRS event.

The new QRS circuit is used in conjunction with a previously existing "V-fib" circuit which identifies QRS complexes and the oscillatory signals associated with ventricular fibrillation, generally represented by relative peaks in the waveform, by comparing the electro-cardiac signal to the preceding peak value of that signal. This is done because, while the new QRS detector provides a reliable indication of a QRS complex, it is found to almost completely ignore true ventricular fibrillation.

Based on the characteristics of these two detectors a logic protocol has been devised to more accurately identify three selected types of life threatening cardiac arrhythmia. According to the protocol, if the output of the QRS circuit is greater than or equal to 200 pulses per minute, tachycardia is identified and a defibrillation triggering signal is generated. If both the output of the QRS circuit and the V-fib circuit are less than 25 pulses per minute, then bradycardia is identified and pacing triggering signals are generated. It has been found that in the presence of true ventricular fibrillation the output rate of the QRS detector is always less than half (ordinarily much less) the rate of the output of the V-fib circuit; consequently, according to the protocol, when output of the V-fib circuit is greater than or equal to 200 pulses per minute and the rate of the QRS circuit output is less than half the V-fib rate, then ventricular fibrillation is identified and a defibrillation triggering signal is generated. If the output of the V-fib circuit is greater than or equal to 25 pulses per minute and less than 200 pulses per minute, no treatment is appropriate. No treatment is called for if there is respiration since, based upon medical principles, respiration will cease in a patient experiencing ventricular fibrillation, severe tachycardia or bradycardia. It should be recognized that other secondary criteria indicating the occurrence of such life-threatening cardiac arrhythmia, such as the absence of circulatory profusion, could be used in conjunction with analysis of the electro-cardiac signal without departing from the principles of the present invention.

A period of 12 seconds without breath is required before it is appropriate to trigger the administration of therapeutic current. During this time, in order to increase the accuracy of arrhythmia identification, a check is made for three separate occurrences of tachycardia and/or ventricular fibrillation. The absence of detection of such arrhythmia within 7.2 seconds of a previous detection of such arrhythmia indicates low reliability which causes the system to start over again. Time between identification and application of therapy is minimized by initiating at the time of the second indication of tachycardia or ventricular fibrillation the charging of a storage capacitor for application of defibrillation current. Thus, usually by the time that 12 seconds of no breath has lapsed the capacitor is charged and ready to release its energy for defibrillation, thereby wasting no time between arrhythmia identification and therapy.

Accordingly, it is a principle object of the present invention to provide a new and improved cardiac arrhythmia analysis method and apparatus.

It is another object of the present invention to provide a novel method and electronic system for identifying a QRS complex in an electro-cardiac signal.

It is another object of the present invention to provide such an arrhythmia analysis method and apparatus that employs a comparison of the sum of the derivative of the electro-cardiac signal and the low-pass filtered absolute value of the electro-cardiac signal with a reference level, and a comparison of the low-pass filtered electro-cardiac signal with a threshold level to produce a reliable indication of a QRS complex.

It is yet another object of the present invention to provide a logic protocol suitable for utilizing the aforementioned novel QRS identification method and a previously existing electro-cardiac signal analysis technique to arrive at an accurate identification of tachycardia, bradycardia, and ventricular fibrillation.

It is a further object of the present invention to provide a logic system that increases the probability of correct arrhythmia identification and minimizes the time lost between identification and triggering the application of therapeutic current.

The foregoing and other objectives, features and advantages of the present invention will be more readily understood upon consideration of the following detailed description of the invention taken in conjunction with the accompanying drawing.

DETAILED DESCRIPTION OF THE PREFERRED EMBODIMENT

The preferred embodiment of the present invention employs an electronic system for receiving an electrical signal representative of cardiac electrical activity, that is, an electro-cardiac signal, as well as a signal indicative of the presence or absence of respiration, analyzing the two signals, and producing as outputs, signals suitable for triggering or inhibiting the application of therapeutic current to the patient from whom the electro-cardiac and respiration signals were obtained. An electro-cardiac signal with which the system will work is that which is obtained from the tongue to chest-abdominal pathway employed by the apparatus described in U.S. Pat. No. Re. 30,750, which is substantially the same as the signal obtained from a standard Lead II electrocardiogram configuration; however, the system will work with electro-cardiac signals derived from different electrocardiogram configurations, and the invention herein is not limited to a particular electro-cardiac signal.

The system employs a previously-existing circuit for detecting cardiac electrical activity and generally either producing an output pulse in response to the occurrence of a QRS complex or repetitively producing output pulses in responses to the occurrence of ventricular fibrillation. This circuit is referred to herein as the "V-fib" circuit, and is characterized by its tendency to produce twice as many pulses as appropriate in response to the occurrence of some unusual QRS complexes in the electro-cardiac signal, typically those with relatively large "T" wave portions. ("Fine" ventricular fibrillation, that is, low level ventricular fibrillation that is not electrically convertible without the addition of drugs or other medical assistance, is not generally detected and is not considered within the meaning of "ventricular fibrillation" as used herein.) The preferred embodiment also employs a new electro-cardiac analysis circuit which more reliably detects the occurrence of a QRS complex and produces an output pulse in response thereto, while almost completely ignoring true ventricular fibrillation. This is referred to herein as the "QRS circuit."

Based upon the assumptions that a heart beat rate of greater than or equal to 200 beats per minute is excessively high, that a heart beat rate of less than 25 beats per minute is excessively low, and that a V-fib circuit output pulse rate of greater than or equal to 200 pulses per minute is ordinarily indicative of ventricular fibrillation, the preferred embodiment is adopted to trigger appropriate therapeutic current, in the absence of respiration, according to the protocol shown in Table 1.

TABLE 1

LOGIC PROTOCOL

| Circuit/Output Rate* | Physiological Condition | Therapeutic Treatment |
|---|---|---|
| QRS AND V-fib <25 | bradycardia | pacing current |
| QRS ≧200 | tachycardia | defibrillation current |
| $\left(QRS < \frac{V\text{-fib}}{2}\right)$ AND (V-fib ≧200) | ventricular fibrillation | defibrillation current |
| (25 ≦ V-fib <200) AND (QRS <200) | | no treatment |

*The rate is stated in pulses per minute.

Figures 1A, 1B:
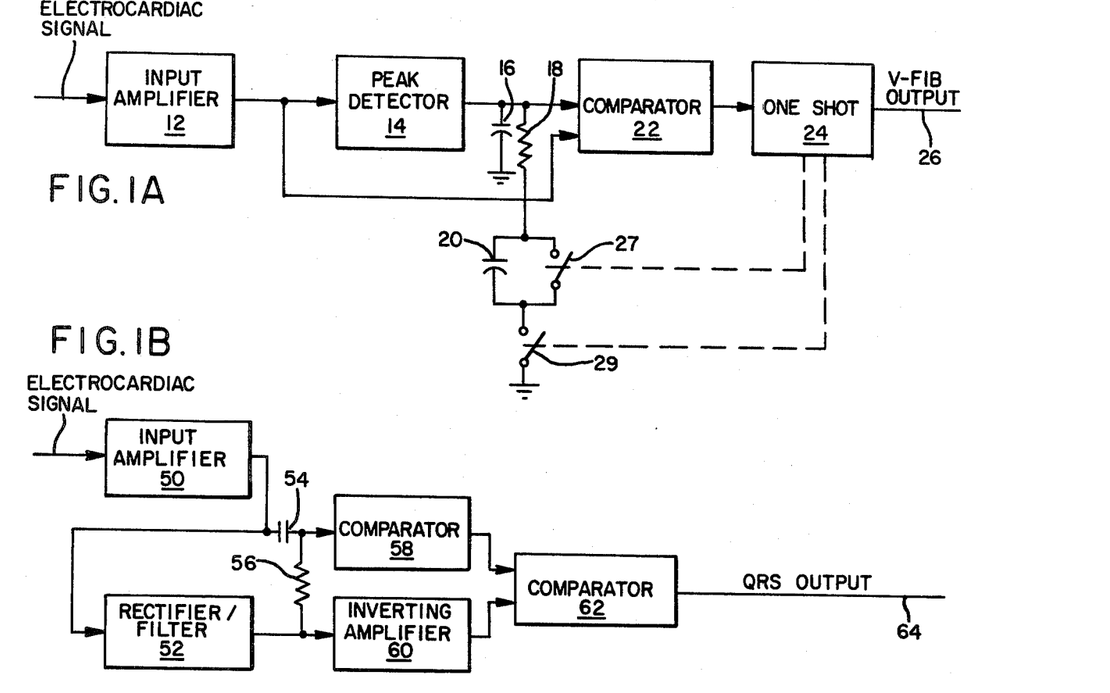
FIG. 1A is a block diagram of a V-fib circuit portion of a preferred embodiment of a cardiac arrythmia analysis system according to the present invention.
FIG. 1B is a block diagram of a QRS circuit portion of the preferred embodiment of the present invention.

Turning now to FIG. 1A, showing a block diagram of the aforementioned prior art V-fib circuit portion of the arrhythmia analysis system, the electro-cardiac signal is received and amplified by a band limited negative-clipping ac input amplifier 12, having a frequency passband of approximately 1–30 Hz. The output from the amplifier 12, which is a positive signal whose amplitude is determined by the input negative slope and amplitude, is rectified by a peak detector circuit 14, and the peak value is stored by a capacitor 16. The capacitor 16 is connected to the inverting input of a comparator 22, the output of the amplifier 12 being connected to the non-inverting input of the comparator, thereby providing variable threshold based on the previously-detected peak value. The output of the comparator triggers a monostable multi-vibrator ("one shot") 24 which produces a "V-fib pulse" at output 26. Resetting of the peak detector occurs when the V-fib output 26 is "high". Switch 27 (actually a pair of MOSFETS) is "open" and switch 29 (also a MOSFET) is "closed", which discharges capacitor 16 through resistor 18 into capacitor 20 for the period of time of the output pulse, as determined by the period of the one-shot 24. This reduces the voltage stored on capacitor 16 by about 40%. When the V-fib output is "low", switch 27 is "closed" and switch 29 is "open", which completely discharges capacitor 20 and allows capacitor 16 to discharge at a relatively slower rate determined by resistances in the comparator 22.

Figure 2:
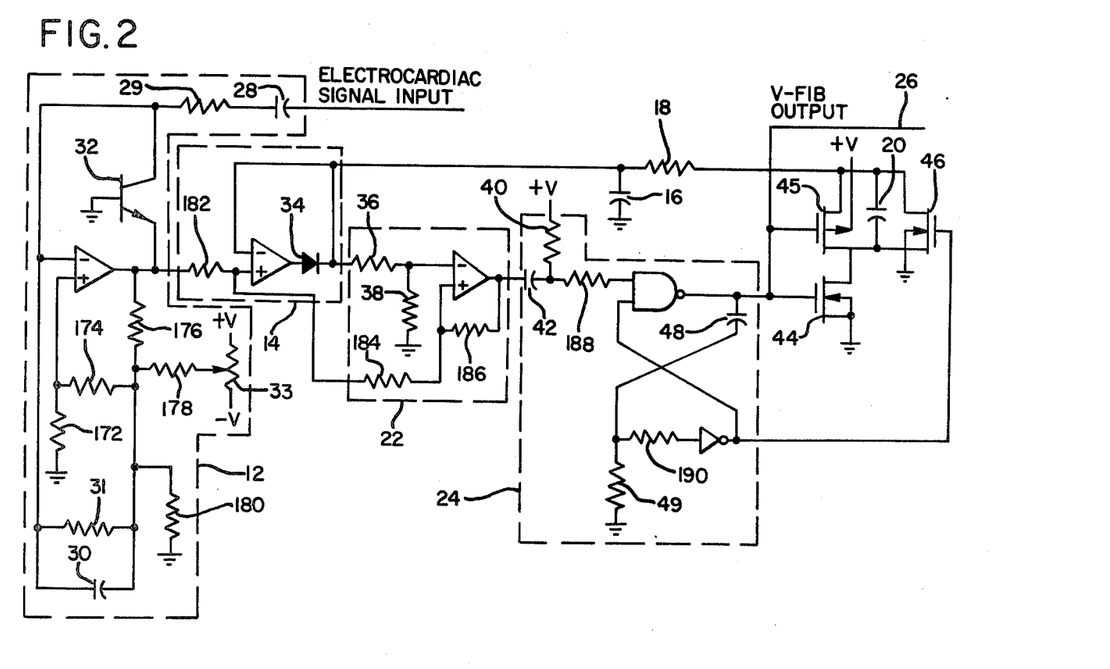
FIG. 2 is a schematic diagram of the aforementioned V-fib circuit of the preferred embodiment.

Referring now to the schematic diagram of the V-fib circuit shown in FIG. 2, the input amplifier 12 has a low frequency cutoff determined primarily by capacitor 28 and resistor 29, and a high frequency cutoff determined primarily by capacitor 30 and resistor 31. Transistor 32 clips higher amplitude positive input signals, while variable resistor 33 provides a bias level adjustment.

In the peak detector 14 the positive signal from amplifier 12 is rectified by diode 34 to charge capacitor 16, which generally discharges through resistors 36 and 38 of the comparator 22. When the output of amplifier 12 exceeds a fixed proportion of the value stored by capacitor 16, the comparator 22 produces a positive-going output. The output 26 of the one shot 24 is normally low due to the bias resistor 40. However, the negative-going output from the comparator triggers the one shot via capacitor 42, which not only produces the V-fib output pulse, but resets the peak detector by turning on MOSFET 44 (corresponding to switch 29) and turning off MOSFETS 45 and 46 (corresponding to switch 27), for a period of time determined by capacitor 48 and resistors 49 and 190.

Some typical values for components in a V-fib circuit of the type described herein are shown in Table 2 hereof.

TABLE 2

SOME TYPICAL COMPONENT VALUES IN THE V-FIB CIRCUIT

| Component | Value |
|---|---|
| 16 | 1 mfd |
| 18 | 10K ohms |
| 20 | .39 mfd |
| 28 | .22 mfd |
| 29 | 100K ohms |
| 30 | .22 mfd |
| 31 | 100K ohms |
| 33 | 100K ohms |
| 36 | 390K ohms |
| 38 | 910K ohms |
| 40 | 1M ohms |
| 42 | .001 mfd |
| 48 | .1 mfd |
| 49 | 1.5M ohms |
| 172 | 130K ohms |
| 174 | 100K ohms |
| 176 | 100K ohms |
| 178 | 511K ohms |
| 180 | 511 ohms |
| 182 | 10K ohms |
| 184 | 33K ohms |
| 186 | 3.9M ohms |
| 188 | 100K ohms |
| 190 | 100K ohms |

Figure 3A:
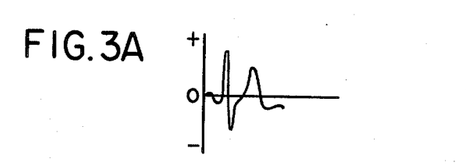
FIGS. 3A–E are exemplary signal waveforms occurring at various points of the QRS circuit portion of the preferred embodiment shown in FIG. 1B.
Figure 3B:
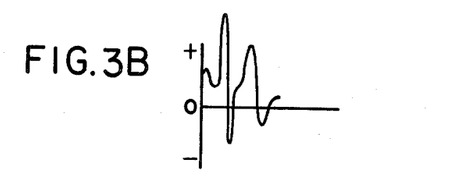

Turning now to FIG. 1B, the QRS circuit also receives the electro-cardiac signal and amplifies and filters it by an ac input amplifier 50 having a passband of about 1–30 Hz. Representative waveforms of a normal electro-cardiac signal and of the output of amplifier 50 are shownl in FIGS. 3A and 3B, respectively.

Figure 3C:
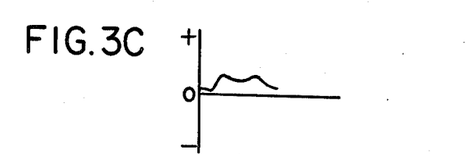

A signal representing the low-pass filtered absolute value of the filtered electro-cardiac signal, illustrated by the waveform in FIG. 3C, is produced by a full-wave rectifier and low-pass filtering circuit 52. A circuit of this type was previously known and described at pp. AN20-8 and -9 of the National Semiconductor *Linear Applications Handbook* (1980). As can be seen by the waveform in FIG. 3C, a normal QRS complex causes the output of the rectifier and filtering circuit 52 to rise rather sharply and peak in the vicinity of the RS transition and thereafter decrease, typically rising again somewhat upon the occurrence of a T wave.

The filtered electro-cardiac signal is differentiated by capacitor 54, whose resultant current is summed with a scaled current through resistor 56 derived from the low-pass filtered absolute value of the same electro-cardiac signal. This current sum is presented to a comparator 58, which is referenced to signal ground. The output of this comparator is determined by the direction of input current to the comparator, that is, when the differentiated electro-cardiac signal current is negative and exceeds the amplitude of the scaled, low-pass filtered absolute value current, which is necessarily positive, then the comparator output will swing high, being limited in voltage by a zener diode feedback loop.

Figure 3D:
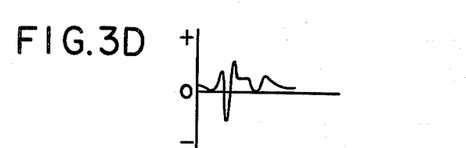
Figure 3E:
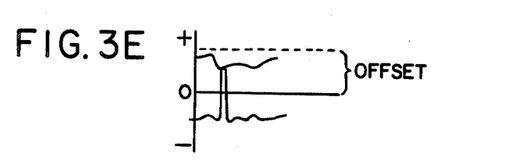

As shown by the waveform in FIG. 3D, for a normal QRS complex the negative-going R-S transition produces a distinct negative dip in the waveform representing the sum of these two signals, which triggers comparator 58, thereby producing the bottom waveform shown in FIG. 3E. In the case of a ventricular fibrillation signal, however, the relative magnitudes of the differentiated electro-cardiac signal and the rectified and filtered electro-cardiac signal are such that a negative current sum capable of triggering the comparator is only infrequently produced.

The rectified and filtered electro-cardiac signal is inverted by inverting amplifier 60, which also provides an adjustable amount of gain and offset. The output of the comparator 58 is then compared to the rectified and filtered electro-cardiac signal by comparator 62. The output of comparator 58 is input to the non-inverting input of the comparator 62. The output of the inverting amplifier 60 is input to the inverting input of the comparator 62. Consequently, the output of comparator 58, essentially a pulse of predetermined amplitude, is compared to an inverted, offset rectified and filtered electro-cardiac signal, as shown by the waveforms in FIG. 3E.

It has been found that a reliable indication of the occurrence of a QRS complex is the existence of a condition where the total of the comparator 58 output signal plus the rectified and filtered electro-cardiac signal, less a predetermined offset value is greater than zero. This is illustrated by the waveforms shown in FIG. 3E wherein the lowest dip of the downwardly extending envelope of the inverted and offset average energy signal, which coincides generally with the occurrence of an R-S transition, overlaps the upwardly extending envelope of comparator 58 output, which also coincides generally with an R-S transition. This produces a pulse at the QRS output 64 from the comparator 62. Since the output of the comparator 58 is a pulse of fixed amplitude, the effect is to produce a QRS pulse when the sum of the derivative of the electro-cardiac signal plus the rectified and filtered electro-cardiac signal is negative, and the rectified and filtered electro-cardiac signal exceeds a threshold level. In the case of ventricular filtration the rectified and filtered electro-cardiac signal does not typically dip down in the same manner and output pulses are not usually produced by the comparator 58.

Figure 4:
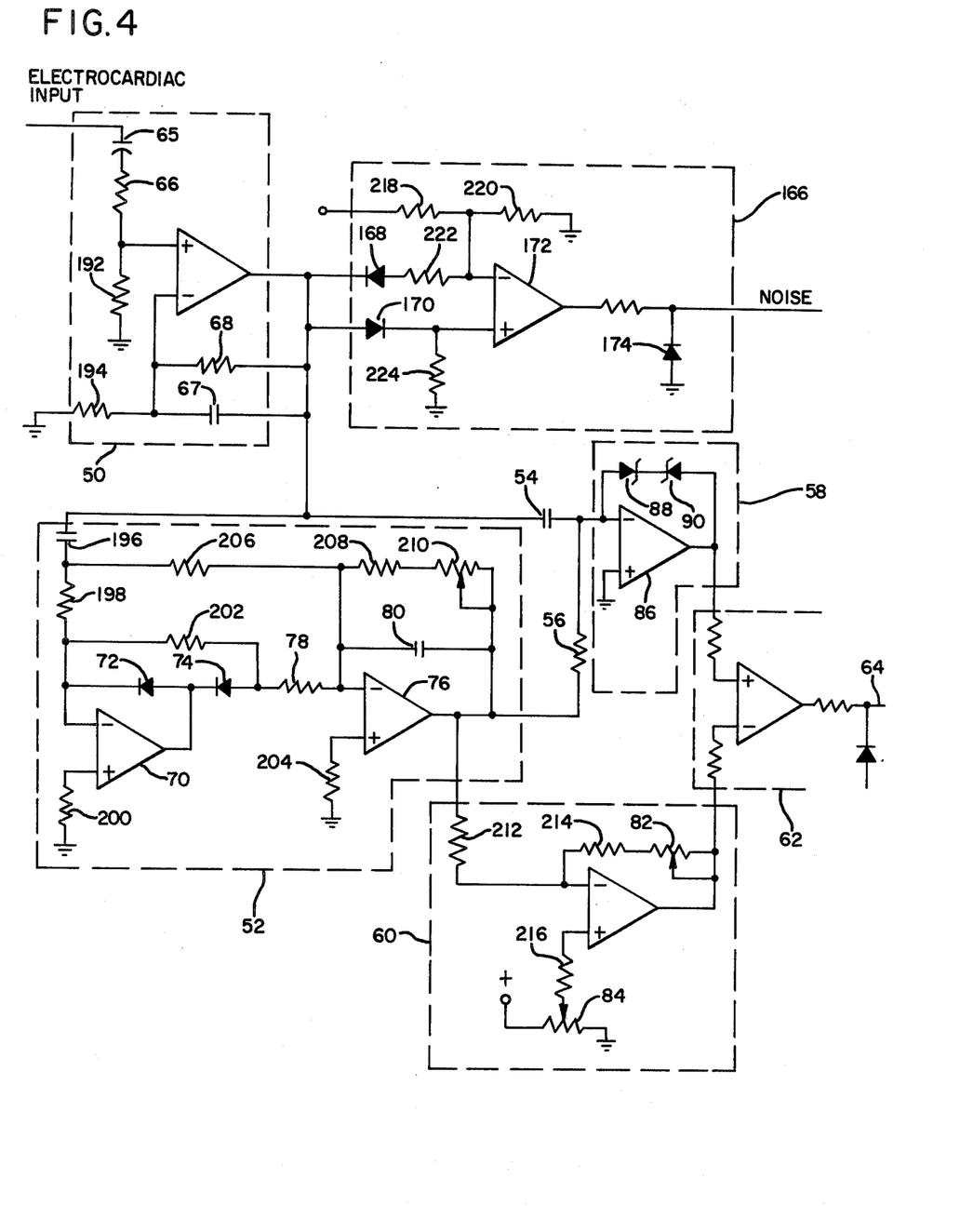
FIG. 4 is a schematic diagram of the aforementioned QRS circuit of the preferred embodiment.

A schematic diagram of a QRS circuit according to the preferred embodiment is shown in FIG. 4. In the input amplifier 50, the low frequency cut off is determined primarily by capacitor 65 and resistor 66. The high frequency cutoff is determined primarily by capacitor 67 and resistor 68.

The rectifier and averaging circuit 52 employs a full-wave rectifier comprising basically amplifier 70 and diodes 72 and 74, and a low-pass filter comprising basically amplifier 76, resistor 78 and capacitor 80. The output is inverted by the inverting amplifier 60, which has in variable resistor 82 a gain control and in variable resistor 84 an output offset control.

Differentiation is accomplished by capacitor 54. The comparator 58 employs an amplifier 86 with back-to-back zener diodes 88 and 90 in a negative feedback loop. These diodes limit the positive and negative voltage excursions of the comparator output, thereby ensuring that a pulse resulting from a QRS complex will have predetermined amplitude.

Some typical values for components in a QRS circuit of the type described herein are shown in Table 3 hereof.

TABLE 3
SOME TYPICAL COMPONENT VALUES
IN THE QRS CIRCUIT

| Component | Value |
|---|---|
| 54 | .01 mfd |
| 56 | 1M ohm |
| 65 | .22 mfd |
| 66 | 10K ohms |
| 67 | .01 mfd |
| 68 | 1M ohm |
| 78 | 100K ohms |
| 80 | .68 mfd |
| 82 | 10K ohms |
| 84 | 10K ohms |
| 192 | 1M ohm |
| 194 | 10K ohms |
| 196 | .47 mfd |
| 198 | 200K ohms |
| 200 | 100K ohms |
| 202 | 200K ohms |
| 204 | 47K ohms |
| 206 | 200K ohms |
| 208 | 100K ohms |
| 210 | 100K ohms |
| 212 | 10K ohms |
| 214 | 5.1K ohms |
| 216 | 10K ohms |
| 218 | 15K ohms |
| 220 | 56K ohms |
| 222 | 10K ohms |
| 224 | 10K ohms |

Figure 1C:
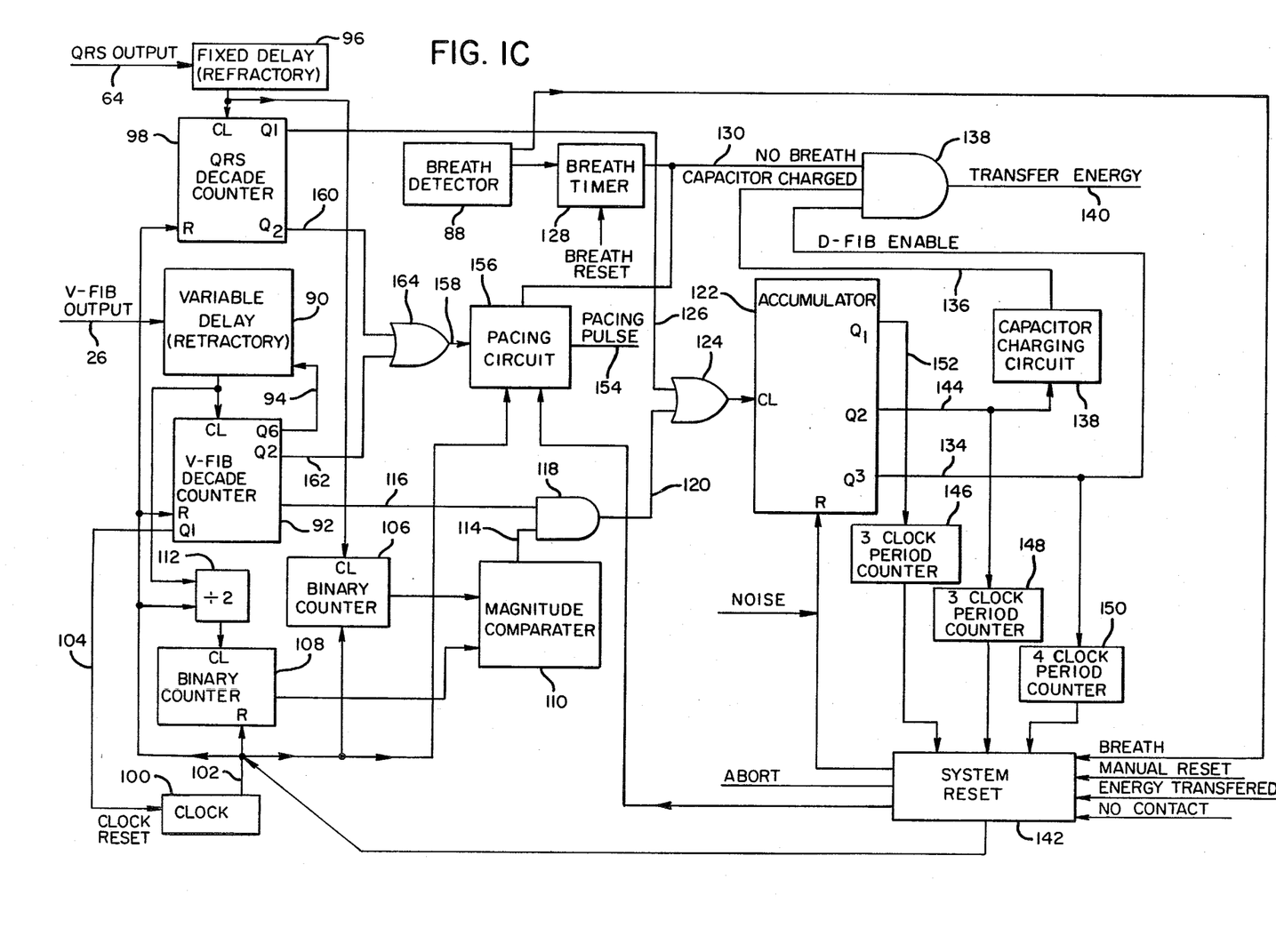
FIG. 1C is a block diagram of a logic portion of the preferred embodiment of the present invention and of related functions.

Referring to FIG. 1C, diagnosis of cardiac arrhythmia is accomplished by a logic circuit based on the QRS and V-fib outputs 64 and 26, respectively, and on the output from a breath detector 88. Suitable devices for detecting the presence or absence of respiration and producing an electrical signal representative thereof are known in the art, for example, the circuit shown in FIG. 10 of U.S. Pat. No. Re. 30.750. The V-fib output 26 is applied to a variable delay circuit 90 which provides a refractory period for triggering of the logic circuit input by the V-fib signal; that is, once triggered by V-fib output, the logic circuit will require a predetermined period of time before it can be triggered again by a V-fib pulse.

The refractory period provided by the variable delay circuit 90 prevents double counting of QRS complexes at rates of less than 200 beats per minute. This is needed because of the tendancy of the V-fib circuit to double count in response to unusual QRS complexes. The refractory period is ordinarily long enough that the logic circuit can only be triggered once for each heart beat. At higher heart beat rates of 125 beats per minute or more the refractory period is reduced to ensure that each QRS complex can be counted and that ventricular fibrillation can be properly detected.

The output of the variable delay circuit 90 is input to a V-fib decade counter 92 which counts the number of V-fib pulses during a predetermined rate-measurement period to arrive at a V-fib rate. Upon the occurrence of a rate of at least 125 pulses per minute, a signal is returned to the variable delay circuit 90 via line 94 to decrease the refractory period.

Similarly, the QRS output 64 is received by a fixed delay circuit 96, which provides a refractory period for QRS input triggering. This is also needed to prevent double counting of QRS complexes, in this case to permit triggering on a pulse resulting from the negative-going edge of a Q wave or of an R wave, but not both. The output of delay circuit 96 is input to a QRS decade counter 98, which determines the QRS pulse rate based on the same measurement period.

The measurement period is determined by a clock 100 which generates clock pulses at its output 102 at a predetermined rate, preferably 2.4 seconds, though a different period might be used. The clock output 102 resets, among other things, the V-fib counter 92 and the QRS counter 98 to start a new rate measurement. In order to increase accuracy, the clock is synchronized to the V-fib counter so that when a V-fib pulse first occurs the clock will reset and begin the measurement period to establish the V-fib pulse rate. To this end an output 104 representing the least significant bit of the decade counter 92 is provided to the clock circuit 100.

Figure 5A:
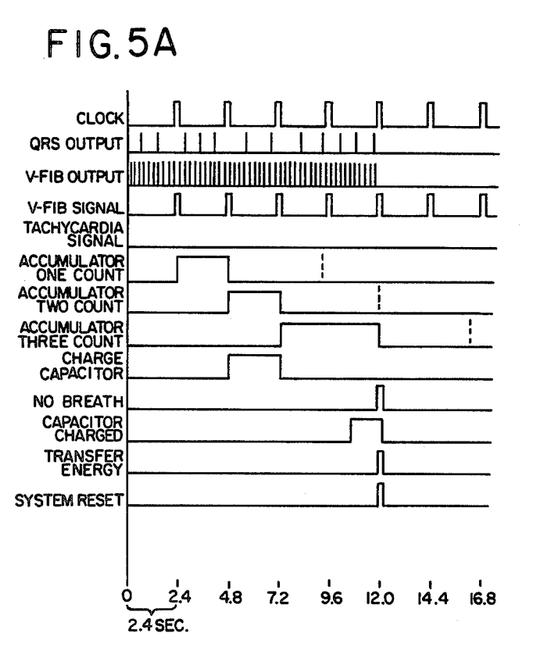
FIGS. 5A–C are exemplary timing diagrams representing logic signals occurring in the logic portion of the preferred embodiment.

General operation of the logic circuit is conveniently explained starting with the sequence of events leading to identification of ventricular fibrillation and a request for defibrillation, as illustrated by the timing diagram of FIG. 5A. The V-fib circuit would be producing output pulses at a rate of greater than or equal to 200 pulses per minute, the QRS circuit would be producing pulses at less than half that rate at most, and the clock would be generating clock pulses every 2.4 seconds following the first V-fib pulse.

Comparison of the QRS rate to the V-fib rate is accomplished by binary counters 106 and 108, and a digital magnitude comparator 110. The output of the QRS delay circuit 98 is received by binary counter 106 which counts QRS pulses. The output of the V-fib delay circuit 90 is received by a divide-by-two circuit 112, whose output is received by the binary counter 108, which counts every other V-fib pulse. Counters 106 and 108, and divide-by-two circuit 102 are all reset by the clock pulse output 102. The count outputs of counters 106 and 108 are received by respective inputs of the magnitude comparator 110 which issues a true output 114 when the magnitude of the binary count in the counter 108 exceeds the count in the counter 106, indicating that the QRS pulse rate is less than half the V-fib pulse rate.

If the 2.4 second measurement period should pass without the receipt by the V-fib counter 92 of at least nine V-fib pulses, the first having reset the measurement period, all of the measurement counters 92, 98, 106, and 108 will be reset by the clock. This means that both the QRS rate and the V-fib rate are less than 200 pulses per minute, since the V-fib circuit will count QRS complexes and produce a rate at least as high as the rate produced by the QRS circuit. On the other hand, if eight V-fib pulses occur by the end of the measurement period, a true signal will be issued on output 116 from the nine-count output of the counter 92, indicating the occurrence of ventricular fibrillation, provided that the QRS rate is less than half of the V-fib rate, as indicated by a true signal on the output 114 of the magnitude comparator 110. With both outputs 114 and 116 true, AND circuit 118 issues a true "ventricular fibrillation" signal on output 120 which is received by an accumulator 122 through an OR circuit 124, thereby causing the accumulator to advance one count. Each subsequent true ventricular fibrillation signal on output 120 advances the accumulator another count. Upon the timely receipt of three such signals, the logic circuit issues a request for defibrillation trigger pulse, provided that within a predetermined period of time it is determined that 12 seconds have elapsed without respiration.

Figure 5B:
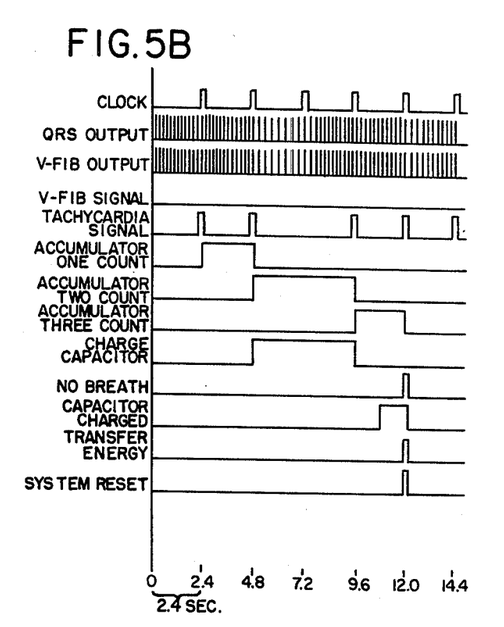

If prior to the end of the measurement period eight QRS pulses are counted by the QRS counter 98, a true "tachycardia" signal will be issued by the nine-count output 126 of the QRS counter and received by the accumulator 122 through the OR circuit 124. As to the remaining circuitry, the occurrence of a tachycardia signal will have the same effect as the occurrence of a ventricular fibrillation signal. This situation is illustrated by the timing diagram in FIG. 5B.

Identification of a 12 second period without breath is accomplished by the breath detector 88 and a resetable breath timer 128 which may be of a variety of types of timing circuits commonly known in the art. If, within the 12 second period from reset of the breath timer (which preferably occurs as the result of power turn on, manual reset, lack of patient-electrode continuity, the transfer of therapeutic energy to the patient, or the occurence of a breath) an absence of breath is detected, a true "no breath" signal is produced at output 130 at the end of that period.

The combination of a true signal from the three-count output 134 of the accumulator 122, a true no breath signal from the breath timer output 130, and a true signal 134 from a capacitor charging in circuit 136 provided for charging a capacitor which provides the energy for defibrillation, indicating that the defibrillation capacitor is charged, AND circuit 138 issues a transfer energy signal 140 requesting the application of defibrillation current by an appropriate defibrillating circuit. Capacitor charging circuits and defibrillating circuits are well known in the art; for example, circuits of the type shown in FIG. 13 of U.S. Pat. No. Re. 30,750, may be used.

Upon the occurrence of a defibrillation current, system reset circuit 142 generates system reset signals which, among other things, clear the accumulator and the measurement counters. The system is also preferably adapted to be reset manually and by the occurrence of a breath and as a result of lack of patient-electrode continuity.

In order to minimize delay from the time of diagnosis until the time of application of a therapeutic current (pacing or defibrillation), the two-count output 144 of the accumulator 122 initiates the charging of the defibrillation capacitor, which typically takes about 7 seconds. Assuming that from the start of a 12 second no-breath period two consecutive ventricular fibrillation or tachycardia pulses occur at the output of OR circuit 124, the defibrillation capacitor will be charged at about the same time that the no breath pulse occurs.

Figure 5C:
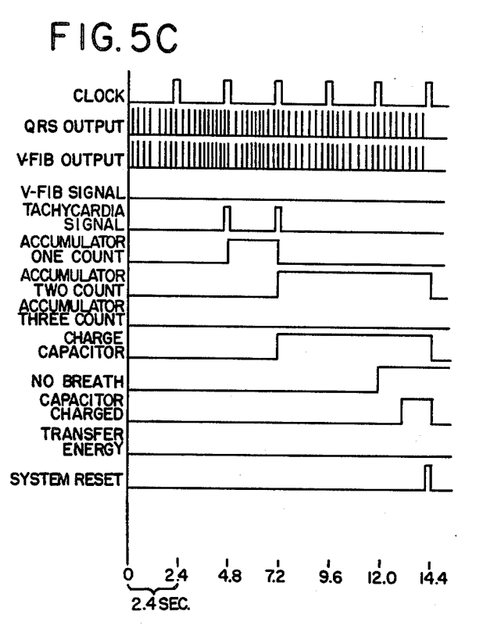

Referring now to FIG. 5C, as well as FIGS. 5A and 1C, the logic circuit is designed so that the failure of a successive ventricular fibrillation or tachycardia pulse to occur within predetermined periods will produce a system reset. This is accomplished by clock period counters 146, 148 and 150 which receive inputs from the one-count, two-count, and three-count outputs, respectively, of the accumulator 122. When the one-count output 152 of the accumulator becomes true, the clock period counter 146 begins counting clock pulses. If the one-count output 152 remains true as long as three clock periods, the clock period counter 146 will cause a system reset to occur. Upon receipt of a true signal from the two-count output 148 of the accumulator, the clock period counter 148 will begin counting clock periods. If the two count should remain true as long as three clock periods, the clock period counter 148 will cause a system reset to be issued. Similarly if the three-count output 134 of the accumulator should remain true as long as four clock pulses, a system reset will be issued. The time-out period for each of these three clock period counters 146, 148 and 150 is illustrated with respect to the beginning of the one-, two- and three-count outputs, respectively, by dashed lines in FIG. 5A. In this manner the logic ensures first, that each of three successive ventricular fibrillation or tachycardia pulses, that is, three "defibrillation request" pulses, must be received within 7.2 seconds of their predeces, and second, that defibrillation occurs within 9.4 seconds of the third pulse, or the system will be reset. If the system is caused to reset after the third defibrillation request pulse it preferably will also issue an "abort" signal which can be used by a defibrillation circuit to trigger internal discharge of the defibrillation capacitor. FIG. 5C shows an exemplary situation where a third pulse was not received within the prescribed period following the second pulse.

Pacing current is provided by the output 154 of pacing circuit 156. Numerous such circuits are known in the prior art, and no particular design is necessary to the operation of the present invention, though the embodiment described herein contemplates a disabling input 158 which prevents pacing and a no breath input 159. If either the QRS decade counter 98 or the V-fib decade counter 92 receives a pulse during the measurement period of 2.4 seconds, the input pulse rate to the respective counter is equal to or greater than 25 pulses per minute. The two-count output 160 of the QRS decade counter, and the two-count output 162 of the V-fib decade counter are used to detect this condition. If either output becomes true, OR circuit 164 issues a disabling signal to the pacing circuit, which prevents the application of a pacing current to the patient. Conversely, in the absence of a true signal from either of the two-count outputs of the counters 98 or 92, a pacing current will be applied to the patient. The preferred embodiment contemplates but the invention does not require, that pacing current will be stimulated by the clock output 102, that is, every 2.4 seconds. Consequently, the combination of a "not true" disable input, the occurrence of a clock pulse, and a no breath signal, triggers a pacing current, though other types of pacing circuits and logic arrangements could be utilized as well.

Referring again to FIG. 4., the system is also provided with an interference detector 166 that resets the accumulator 122 in the presence of interfering signals that may produce QRS and V-fib outputs. The filtered electro-cardiac signal is rectified by diodes 168 and 170, and comparator 172 produces a positive pulse in response to negative or positive electro-cardiac signals of excessive amplitude, thereby resetting the accumulator.

Figure 6A:
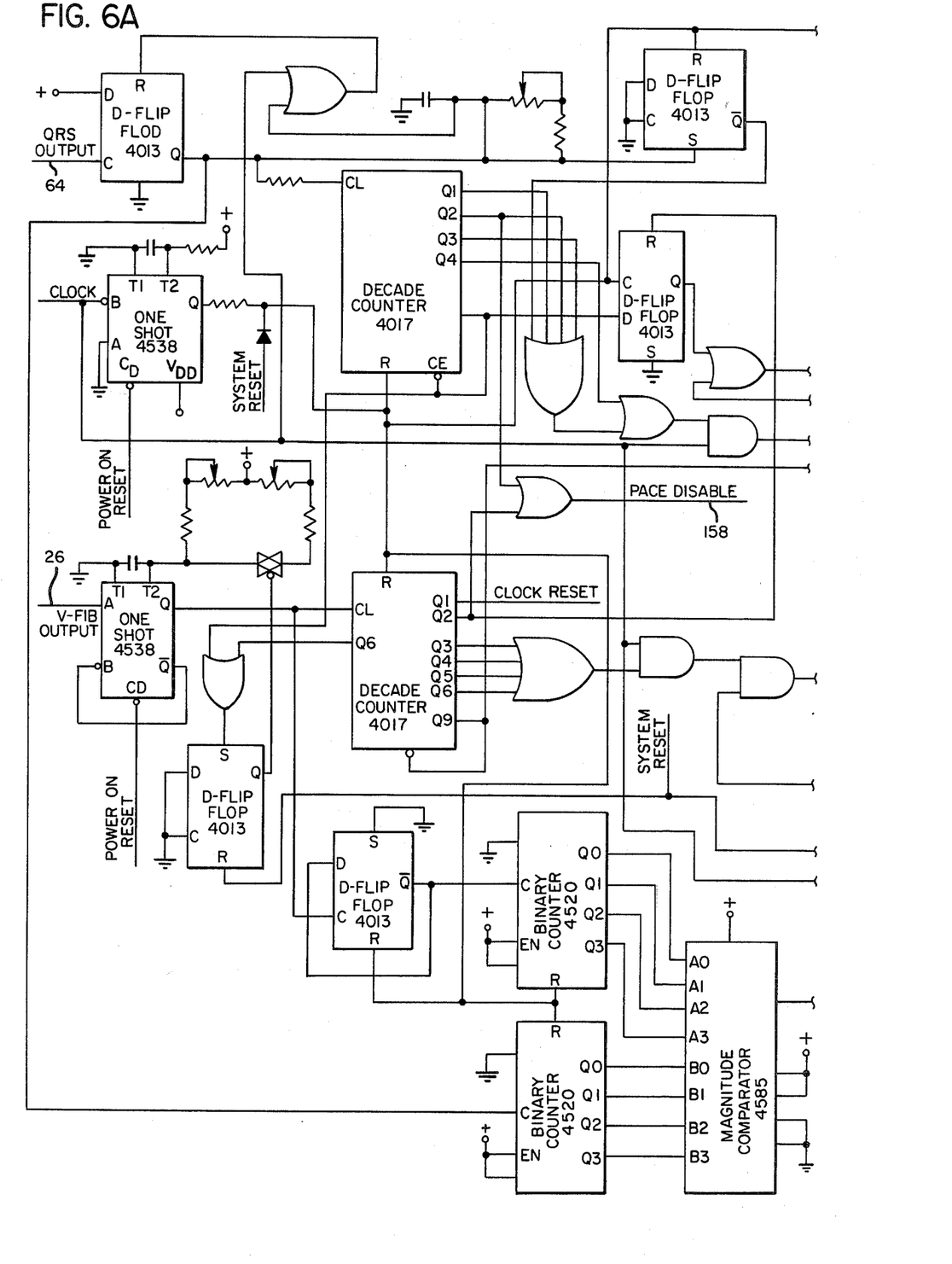
FIGS. 6A and B are schematic diagrams of the aforementioned logic portion of the preferred embodiment.
Figure 6B:
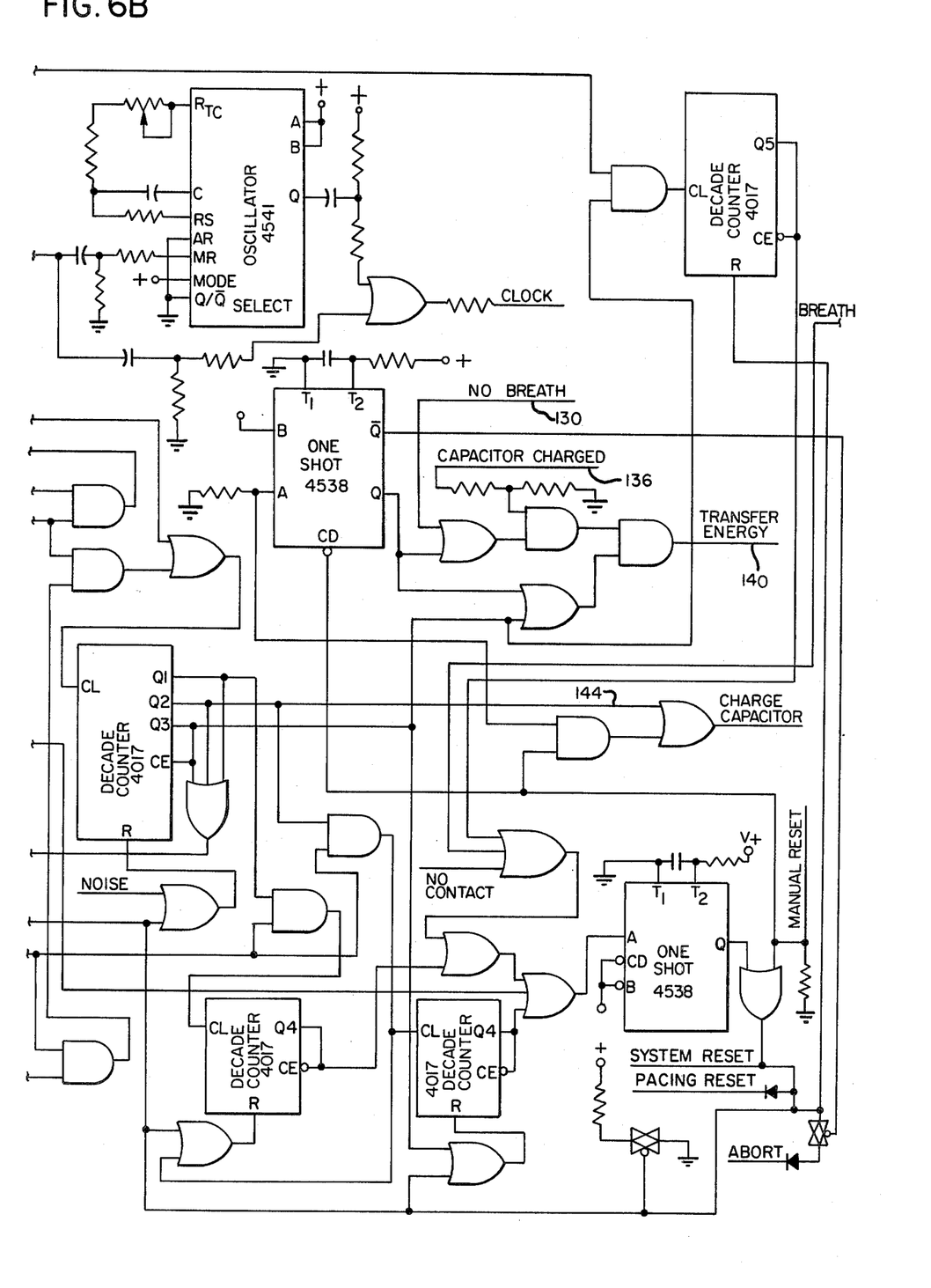

The afore-described logic funtions could be performed by a variety of different logic circuit designs, including a software-driven digital processor, and, while one particularly suitable circuit design is shown in the schematic diagram of FIGS. 6A and 6B, there is no intention herein to limit the scope of the invention to any particular circuit implementation. The characteristics and operation of the components shown in the diagram are commonly known to persons skilled in the art of logic design.

The terms and expressions which have been employed in the foregoing specification are used therein as terms of description and not of limitation, and there is no intention, in the use of such terms and expressions, of excluding equivalents of the features shown and described or portions thereof, it being recognized that the scope of invention is defined and limited only by the claims which follow.

What is claimed is:

1. A system for monitoring the cardiac electrical activity and at least one other selected life sign of a patient, and triggering the application of appropriate therapeutic current to said patient, comprising:
   (a) input means for receiving from said patient an electro-cardiac signal representative of said electrical activity of said patient's heart and a second signal derived from said other selected life sign and indicative of a second criterion for the identification of selected cardiac arrhythmia;
   (b) V-fib circuit means, responsive to said electro-cardiac signal, for repetitively producing V-fib pulses at a rate greater than or equal to a first predetermined rate in response to the occurrence of ventricular fibrillation and for producing at least one V-fib pulse in response to the occurrence in sid electro-cardiac signal of a QRS complex;
   (c) QRS circuit means, responsive to said electro-cardiac signal, for producing a QRS pulse in response to the occurrence in said electro-cardiac signal of a QRS complex while producing in response to ventricular fibrillation QRS pulses at less than half the rate of V-fib pulses produced by said V-fib circuit means; and
   (d) logic means, for producing a defibrillation trigger signal, said logic means having clock means for establishing a rate measurement period, means for counting the number of QRS and V-fib pulses during said rate measurement period to determine the respective rates thereof and for producing a defibrillation request pulse if, during said rate measurement period, either the number of V-fib pulses equals or exceeds said first predetermined rate while the number of QRS pulses is less than half the V-fib pulse rate or the number of QRS pulses equals or exceeds said first predetermined rate, accumulator means responsive to said defibrillation request pulse for counting the number of said request pulses during an accumulation period, and output means, responsive to said timing means and to said second signal for producing a defibrillation trigger signal upon the occurrence of three defibrillation pulses within said accumulation period and of said second criterion for a predetermined period.

2. The system of claim 1, wherein said other selected life sign is respiration, said second criterion being the absence thereof.

3. A method for determining whether or not to defibrillate a patient based upon the identification of apparent ventricular fibrillation, represented by a fibrillation pulse or tachycardia represented by a tachycardia pulse, from analysis of cardiac electrical activity during a predetermined measurement period, comprising:

(a) requiring the identification of three occurrences of either defibrillation or tachycardia pulses and no respiration within a first period in order to fibrillation;
(b) restarting said first period if following a first identification a second identification does not occur within a second predetermined period;
(c) restarting said first period if following said second identification a third identification does not occur within a third predetermined period;
(d) restarting said first period if for a fourth predetermined period following said third identification there has been respiration during a preceeding fifth predetermined period, the total of said second, third and fourth periods equalling said first period.

* * * * *

UNITED STATES PATENT AND TRADEMARK OFFICE
CERTIFICATE OF CORRECTION

PATENT NO. : 4,473,078
DATED : September 25, 1984
INVENTOR(S) : James H. Angel

It is certified that error appears in the above-identified patent and that said Letters Patent is hereby corrected as shown below:

Col. 2, Line 54  Change "lowpass" to --low-pass--;

Line 56  After "less" change "that" to --than--;

Line 63  Change "if" to --is--.

Col. 4, Line 64  Change "responses" to --response--.

Col. 5, that portion of TABLE 1 reading

" $\left\{ QRS < \frac{V\text{-}fib}{2} \right\}$ AND  ventricular  defibrillation (V-fib $\geq$ 200)  fibrillation  current"

should read:

--(QRS < $\frac{V\text{-}fib}{2}$) AND  ventricular  defibrillation
(V-fib $\geq$ 200)  fibrillation  current--.

UNITED STATES PATENT AND TRADEMARK OFFICE
CERTIFICATE OF CORRECTION

PATENT NO.  : 4,473,078

DATED       : September 25, 1984

INVENTOR(S) : James H. Angel

It is certified that error appears in the above-identified patent and that said Letters Patent is hereby corrected as shown below:

| | |
|---|---|
| Col. 6, Line 54 | Change "shown1" to --shown--. |
| Col. 7, Line 54 | Change "filtration" to --fibrillation--. |
| Col. 8, Line 48 | Change "30.750" to --30,750--. |
| Col. 11, Line 19 | Change "predeces" to --predecessor--. |
| Col. 12, Line 31 | Change "sid" to --said--. |
| Col. 13, Line 2 | Change "defibrillation" to --fibrillation--; |
| Line 3 | Change "fibrillation" to --defibrillate--. |

Signed and Sealed this

Seventeenth Day of December 1985

[SEAL]

Attest:

DONALD J. QUIGG

Attesting Officer

Commissioner of Patents and Trademarks